United States Patent
Oh et al.

(10) Patent No.: US 9,963,696 B2
(45) Date of Patent: May 8, 2018

(54) METHOD FOR SCREENING MUTANT MICROORGANISM OVERPRODUCING TARGET METABOLITE USING SYNTHETIC SUICIDE GENETIC CIRCUIT

(71) Applicant: Korea University Research and Business Foundation, Seoul (KR)

(72) Inventors: Min-Kyu Oh, Gyeonggi-do (KR); Sang-Woo Lee, Gyeonggi-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 716 days.

(21) Appl. No.: 14/515,408

(22) Filed: Oct. 15, 2014

(65) Prior Publication Data
US 2015/0376610 A1 Dec. 31, 2015

(30) Foreign Application Priority Data
Jun. 30, 2014 (KR) ................ 10-2014-0080955

(51) Int. Cl.
*C12N 15/10* (2006.01)
*C12N 9/10* (2006.01)
*C07K 14/715* (2006.01)
*C07K 14/745* (2006.01)

(52) U.S. Cl.
CPC ........ *C12N 15/1079* (2013.01); *C07K 14/715* (2013.01); *C07K 14/745* (2013.01); *C12N 9/1096* (2013.01); *C12Y 206/01016* (2013.01); *C07K 2319/10* (2013.01); *C07K 2319/55* (2013.01); *C07K 2319/60* (2013.01)

(58) Field of Classification Search
None
See application file for complete search history.

(56) References Cited

PUBLICATIONS

Yang et al ("Synthetic RNA devices to expedite the evolution of metabolite-producing microbes". Nat Commun 2013 vol. 4: p. 1413). (Year: 2013).*
Kang et al (Appl Microbiotechnol 2014 vol. 98, pp. 3413-3424, published Feb. 12, 2014) (Year: 2014).*
Dietrich, J., et al., "High-Throughput Metabolic Engineering: Advances in Small-Molecule Screening and Selection", "Annu. Rev. Biochem.", Apr. 2, 2010, pp. 563-590, vol. 79.
Lee, S., et al., "2013 KSBB Fall Meeting and International Symposium Presentation and Poster", Oct. 16-18, 2013, pp. 1-46, Published in: Busan, Republic of Korea.
Lee, S., et al., "2014 KSBB Spring Meeting and International Symposium Program and Poster", Apr. 9-11, 2014, pp. 1-2, Published in: Gyeongju, Republic of Korea.
Lee, S., et al., "2014 ME-X Conference Program Book and Poster", Jun. 15, 2014, pp. 28 and 53, Published in: Vancouver, Canada.
Michener, J., et al., "High-throughput enzyme evolution in *Saccharomyces* cerevisiae using a synthetic RNA switch", "Metabolic Engineering", Apr. 25, 2012, pp. 306-316, vol. 14.
NCBI GeneBank Accession No. NP012818.1, Nov. 10, 1999, pp. 1-7.
Kang, Z., et al., "Small RNA regulators in bacteria: powerful tools for metabolic engineering and synthetic biology", Applied Microbiology and Biotechnology, Feb. 12, 2014, pp. 3413-3424, vol. 98.
Kuznetsova, E., et al., "Genome-wide Analysis of Substrate Specificities of the *Escherichia coli* Haloacid Dehalogenase-like Phosphatase Family", The Journal of Biological Chemistry, Nov. 24, 2006, pp. 36149-36161, vol. 281, No. 47.

* cited by examiner

*Primary Examiner* — Catherine S Hibbert
(74) *Attorney, Agent, or Firm* — Hultquist, LLC; Steven J. Hultquist

(57) ABSTRACT

The present invention relates to a method of screening a target metabolite-overproducing mutant strain using a synthetic suicide genetic circuit, and more particularly to a method of screening only a metabolite-overproducing mutant strain while killing a mutant strain that does not produce the metabolite, by introducing into mutant strains a synthetic suicide genetic circuit comprising a suicide gene coupled with a riboswitch. The method for screening a target metabolite-overproducing mutant strain according to the present invention has advantages in that a metabolite-overproducing mutant strain having a relatively fast or slow growth rate can be separated by visual observation, and in that the riboswitch that is used in the synthetic suicide genetic circuit can be replaced depending on the kind of target metabolite, and thus the synthetic suicide genetic circuit can be applied commonly to various strains.

8 Claims, 6 Drawing Sheets

FIG. 6
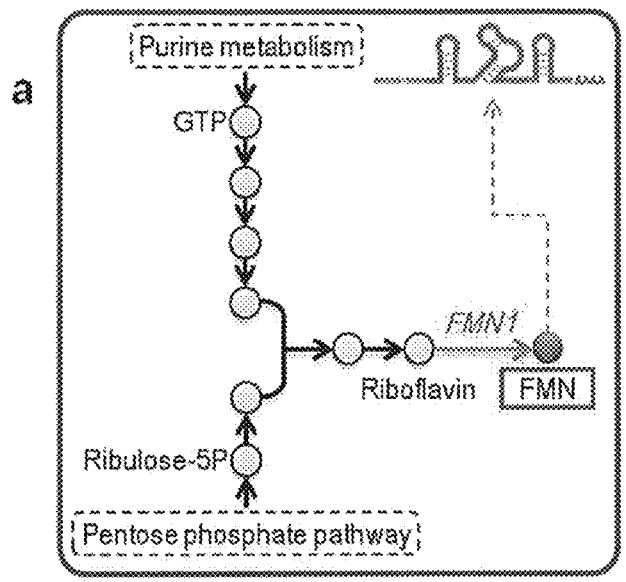
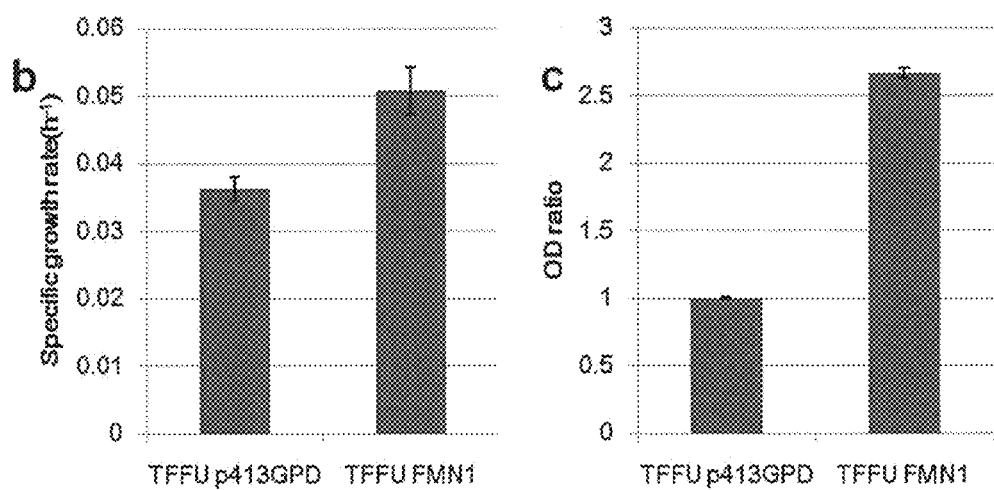

METHOD FOR SCREENING MUTANT MICROORGANISM OVERPRODUCING TARGET METABOLITE USING SYNTHETIC SUICIDE GENETIC CIRCUIT

TECHNICAL FIELD

The present invention relates to a method of screening a target metabolite-overproducing mutant strain using a synthetic suicide genetic circuit, and more particularly to a method of screening only a metabolite-overproducing mutant strain while killing a mutant strain that does not produce the metabolite, by introducing into mutant strains a synthetic suicide genetic circuit comprising a suicide gene coupled with a riboswitch.

BACKGROUND ART

Since a long time ago, cellular metabolisms such as microbial fermentation have been used to process food. However, as the understanding of intracellular mechanisms has been enhanced, it became possible to regulate cellular metabolic pathways using DNA recombination technology and a variety of recently developed new synthetic devices in order to satisfy engineering demands. Synthetic systems can be used without difficulty to introduce phenotypic perturbation, because artificial operations are operated independently of intracellular regulatory systems. Thus, such synthetic systems have the potential to widen the range of accessible phenotypes. As a good example of this case, synthetic riboswitches have been artificially designed and introduced into microorganisms in order to reprogram microbial metabolic pathways according to engineering demands.

Riboswitches are constructs that regulate genes in a small ligand-dependent manner, and have been found in a variety of RNAs.

Natural riboswitches modify their structures in response to the concentration of an intracellular metabolite, in which the metabolite (ligand) binds to sites other then the active site of the riboswitch (allosteric binding) to modify the three-dimensional structure of the RNA, thereby regulating the expression of the gene. As a result, the termination of transcription of the gene occurs faster than normal, or the initiation of translation into protein is prevented, or the degradation rate of mRNA is affected by the modification.

In view of the fact that riboswitches are natural metabolite sensors, a synthetic genetic circuit comprising a synthetic riboswitch can be developed and applied in terms of evolutionary engineering in order to achieve the high-efficiency screening of microorganisms that produce useful metabolites. In order to efficiently screen mutants, which overproduce useful metabolites, from mutants having randomly perturbed phenotypes, the mutants should be capable of showing the change in color as a result of the production of the metabolites such that the phenotype of the mutants can be visually observed, or the mutants should be capable of showing the change in the growth rate according to the production of the metabolites. However, only several kinds of metabolites show natural color development or fluorescence, and most metabolites do not show this phenotype. Due to this limitation, there is a problem in that inefficient screening that requires complex experimental procedures is performed. In order to overcome this limitation when screening invisible phenotypes, several attempts have been made to use synthetic metabolite sensors. Particularly, a synthetic riboswitch coupled with a fluorescence protein reporter was developed, and as demonstrated by fluorescence-activated cell sorting (FACS), this synthetic riboswitch efficiently induces the evolution of the enzyme caffeine demethylase (Michener J K et al., *Metab Eng* 14:306-316, 2012).

However, it was found that screening of mutants showing a fast growth rate shows the highest efficiency (Dietrich J A et al., *Annu Rev Biochem* 79:563-590, 2010). In view of this fact, the present inventors have designed a synthetic genetic circuit showing growth rate dependence. Specifically, the synthetic genetic circuit was designed such that it would be possible to select a mutant that overproduces a target metabolite as a result of the change in the growth rate of cells with a change in the concentration of the metabolite in the cells.

In addition, the present inventors have made extensive efforts to enable this screening principle to be applied to various strains that produce various metabolites, and as a result, have designed a riboswitch-based synthetic suicide genetic circuit based on two general and common cellular mechanisms.

One mechanism is an mRNA degradation mechanism in which a self-cleaving ribozyme is involved. This mechanism has already been applied to many genetic circuits, and it is known that this mechanism can be widely applied not only to eukaryotic cell systems, but also to prokaryotic cell systems.

The other mechanism is a generally known mechanism in which the conversion of fluorocytosine to fluorouracil by cytosine deaminase induces cell death (apoptosis). As is known in the art, this mechanism is because fluorouracil, an analog of uracil, exhibits toxicity in eukaryotic cells and prokaryotic cells, resulting in dysfunction of RNA.

In view of these facts, the present inventors have found that for example, the use of a suicide genetic circuit comprising the ribozyme glmS (which responds to the intracellular concentration of the yeast metabolite glucosamine-6-phosphate (GlcN6P)) inserted into the cytosine deaminase-encoding gene FCY1 makes it possible to efficiently screen only yeast mutants that overproduce GlcN6P, thereby completing the present invention.

DISCLOSURE OF INVENTION

Technical Problem

It is an object of the present invention to provide a method of easily screening a target metabolite-overproducing mutant strain by introducing a suicide genetic circuit into mutant strains.

Technical Solution

To achieve the above object, the present invention provides a method for screening a target metabolite-overproducing mutant strain, the method comprising the steps of: (a) constructing mutant strain libraries that have introduced therein a synthetic suicide genetic circuit containing a suicide gene and a riboswitch and contain mutants of a gene that is involved in the production of the target metabolite; (b) culturing each of the mutant strain libraries; and (c) selecting, from among the cultured mutant strain libraries, a mutant strain having a relatively fast growth rate as the target metabolite-overproducing mutant strain.

The present invention also provides a target metabolite overproducing mutant strain screened according to the above-described method.

The present invention also provides a GFA1 mutant comprising amino acid mutations of Q96H and Q157R in an amino acid sequence of SEQ ID NO: 1.

The present invention also provides a GlcN6P-overproducing mutant strain containing a gene that encodes the GFA1 mutant.

The present invention also provides a method for screening a GlcNAc-overproducing mutant strain, the method comprising the steps of: (a) introducing genes encoding various HAD phosphatases into the above-described GlcN6P-overproducing mutant strain to construct mutant strain libraries; (b) culturing each of the mutant strain libraries; and (c) selecting, from among the cultured mutant strains, a mutant strain having a relatively slow growth rate as the GlcNAc-overproducing mutant strain.

The present invention also provides a GlcNAc-overproducing mutant strain containing a gene that encodes HAD phosphatase YqaB or YihX.

Advantageous Effects

A method for screening a target metabolite-overproducing mutant strain according to the present invention has advantages in that a metabolite-overproducing mutant strain having a relatively fast or slow growth rate can be separated by visual observation, and in that the riboswitch that is used in the synthetic suicide genetic circuit can be varied depending on the kind of target metabolite, and thus the synthetic suicide genetic circuit can be applied commonly to various strains.

BRIEF DESCRIPTION OF THE DRAWINGS

FIG. 6 is a schematic view showing a FMN-overproducing biosynthesis pathway (FIG. 6a), and graphs showing the results of comparing the growth rate of yeast resulting from the intracellular production of FMN in order to verify the operation of a synthetic suicide genetic circuit containing a FMN ribozyme (FIGS. 6b and 6c).

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

In the present invention, a synthetic suicide genetic circuit was designed, which comprises a glmS ribozyme, which responds to the yeast metabolite glucosamine-6-phosphate (GlcN6P), coupled with the FCY1 gene known as a gene that encodes yeast cytosine deaminase. The synthetic suicide genetic circuit was introduced into mutant strain libraries containing a gene (GFA1) that is involved in the production of GlcN6P, and then strains having fast growth rates were screened.

Figure 1:
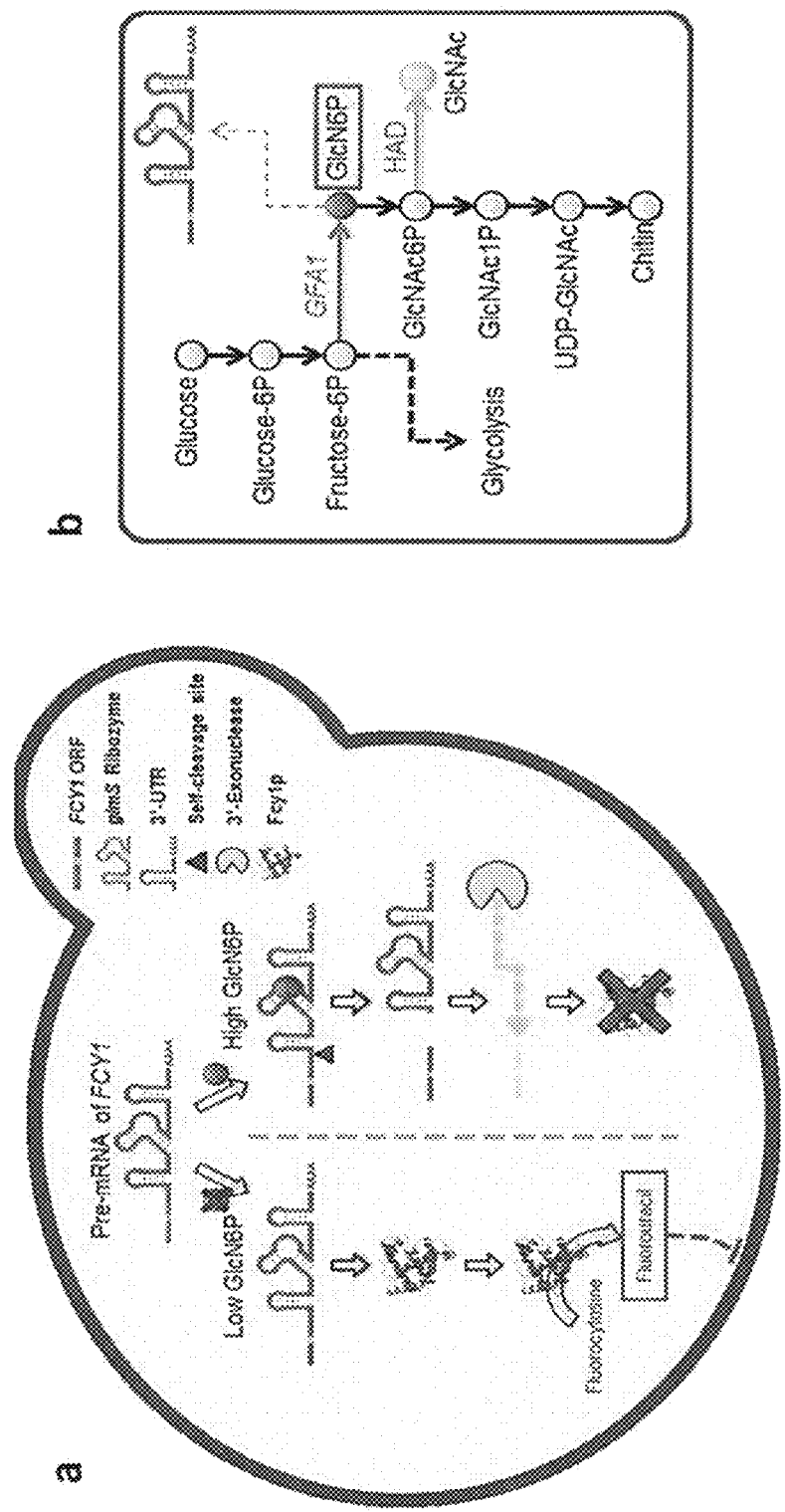
FIG. 1 is a schematic view showing the operation of a synthetic suicide genetic gene containing a glmS ribozyme (FIG. 1a), and a GlcNAc-overproducing biosynthesis pathway (b) used to verify the operation.

As a result, it was shown that, in the case of a mutant strain that produces the metabolite (GlcN6P) in small amount so as not to activate the glmS ribozyme, cytosine deaminase was expressed from the FCY1 gene and converted the externally added fluorocytosine to the toxic substance fluorouracil that kills cells. Also, it was shown that, in the case of a mutant strain that overproduces the metabolite so as to activate the glmS ribozyme, the FCY1 gene was cleaved by enzymatic action, and thus cytosine deaminase was not expressed so that cells normally grew, suggesting that a mutant strain that overproduces the metabolite can be easily screened (FIG. 1).

In addition, it was found that, when a synthetic suicide genetic system comprising a FMN ribozyme in place of the glmS ribozyme, coupled with the FCY1 gene, was introduced into a strain containing a gene (FMN1) that is involved in FMN production, the synthetic suicide genetic circuit normally operated, and thus a mutant strain overproducing the metabolite (FMN; flavin mononucleotide) could be easily screened (FIG. 6a).

Therefore, in one aspect, the present invention is directed to a method for screening a target metabolite-overproducing mutant strain, the method comprising the steps of: (a) constructing mutant strain libraries that have introduced therein a synthetic suicide genetic circuit containing a suicide gene and a riboswitch and contain mutants of a gene that is involved in the production of the target metabolite; (b) culturing each of the mutant strain libraries; and (c) selecting, from among the cultured mutant strain libraries, a mutant strain having a relatively fast growth rate as the target metabolite-overproducing mutant strain.

In the present invention, in a mutant strain that overproduces a target metabolite, the overproduced target metabolite binds to a riboswitch to suppress the synthetic suicide genetic circuit, and in a mutant strain that produces little or no target metabolite, the synthetic suicide genetic circuit operates to induce the death of the mutant strain.

In an example of the present invention, in order to construct a suicide genetic circuit, a vector having a glmS ribozyme-encoding gene inserted therein was amplified and transformed into the FCY1 locus of yeast. As a result, a suicide genetic circuit comprising the glmS ribozyme inserted into the 3'UTR (untranslated region) of pre-mRNA of FCY1 was constructed.

A riboswitch is a construct that forms a portion of mRNA and regulates the translation of mRNA in a small ligand-dependent manner. It binds to an intracellular metabolite serving as a ligand so as to modify the three-dimensional structure of mRNA, thereby regulating the expression of the gene. For example, it allows the termination of gene translation to occur faster than normal, like rho-independent transcription termination, or folds the ribosome-binding site of mRNA so as to prevent the binding of the ribosome, thereby preventing the initiation of translation of mRNA into protein. Also, due to the modification of the RNA structure, it can influence the splicing of pre-mRNA and the degradation rate of mRNA. Thus, the riboswitch regulates the expression of gene in various manners.

Ribozyme is a compound word of 'ribo' of ribonucleic acid (RNA) and 'zyme' of enzyme. Ribozyme having enzymatic activity either acts as a catalyst that promotes reactions with other biomolecules (trans-acting), or acts as an intracellular catalyst that promotes self-ligation or self-cleavage reactions.

A glmS ribozyme is an RNA molecule that is a riboswitch and, at the same time, acts like enzyme. When the ligand metabolite (GlcN6P) acts as an effector molecule to bind to sites other than the active site of a riboswitch (allosteric binding), it is activated by enzyme to undergo a self-cleavage reaction.

In an example of the present invention, the glmS ribozyme used as a component of a suicide genetic circuit self-cleaves its RNA phosphodiester backbone to prevent its translation into protein, when the ligand glucosamine-6-phosphate (GlcN6P) that binds specifically thereto binds to the glmS ribozyme as the concentration thereof increases. Based on this property of the glmS ribozyme, in the present invention, a strain was transformed such that the glmS ribozyme was present on the pre-mRNA of FCY1. Also, when the glmS ribozyme did bind to GlcN6P, it cleaved the ORF (open reading frame) of FCY1, and was degraded by exposure to 3'-exonuclease, so that cytosine deaminase was no longer expressed (FIG. 1a).

In the present invention, the strain may be yeast (Saccharomyces cerevisiae). However, a strain into which a synthetic suicide genetic circuit can be introduced is not limited to yeast, and the synthetic suicide genetic circuit can be introduced into various eukaryotic cells and prokaryotic cells having the ability to produce useful metabolites.

In the present invention, the riboswitch may be a ribozyme that cleaves a suicide gene by enzymatic action after binding to a target metabolite.

In an example of the present invention, the glmS ribozyme was used as a riboswitch integrated into a suicide gene, but is not limited thereto, and can be replaced with a various riboswitches that bind specifically to a target metabolite, depending on the kind of target metabolite. Specifically, it can be replaced with various riboswitches that bind to a ligand selected from the group consisting of cobalamine, cyclic d-GMP, FMN (flavin mononucleotide), glutamine, glycine, lysine, PreQi, purine, SAH (S-adenosylhomocysteine), SAM (S-adenosyl methionine), SAM-SAH, tetrahydrofolate, TPP (thiamine pyrophosphate) and the like, but is not limited thereto.

More specifically, it can be replaced with a ribozyme selected from the group consisting of self-cleavable FMN ribozyme, hairpin ribozyme, hammerhead ribozyme, hepatitis delta virus (HDV) ribozyme, Varkud satellite (VS) ribozyme, beta-globin co-transcriptional cleavage (CotC) ribozyme, twister ribozyme, leadzyme and the like, but is not limited thereto.

More preferably, the ribozyme that is used in the present invention may be the glmS ribozyme that binds to GlcN6P, or a hammerhead allosteric ribozyme that binds to a metabolite to undergo a self-cleavage reaction, like the glmS ribozyme. For example, it can be replaced with a hammerhead allosteric ribozyme that binds to at least one effector molecule selected from the group consisting of FMN, ATP, theophylline, tetracyclin, xanthine, TMPyP4, light and caged theophylline, ERK2 phosphorylated/unphosphorylated, HCV helicase/replicase, Tat protein, cAMP, cCMP, cGMP, 3-methylxanthine, caffeine, aspartame, $Mn^{2+}$, $Fe^{2+}$, $Co^{2+}$, $Ni^{2+}$, $Zn^{2+}$, $Cd^{2+}$, Light and (BDHP-COOH or BCPD-COOH), etc., preferably hammerhead allosteric ribozyme that binds to at least one effector molecule selected from the group consisting of FMN, ATP, theophylline, tetracyclin, xanthine, 3-methylxanthine and caffeine, but is not limited thereto.

In the present invention, the riboswitch may be inserted into the 3' UTR (untranslated region) of pre-mRNA of a suicide gene.

The riboswitch is preferably inserted into the 3' UTR (untranslated region) of pre-mRNA of a suicide gene. Unlike prokaryotic cells, translation in eukaryotic cells is initiated from the start codon AUG, because scanning is initiated from the 5' end. Thus, when the riboswitch is inserted into the 5' UTR, translation will be initiated from an incorrect position, and thus the target suicide gene will not be properly expressed. For this reason, inserting the riboswitch into the 3' UTR is advantageous for efficient instabilization of pre-mRNA.

In the present invention, the suicide gene may be selected from the group consisting of cytosine deaminase-, thymidine kinase-, thymidylate kinase-, uracil phosphoribosyl transferase- and nucleoside diphosphokinase-encoding genes. Examples of suicide genes that may be used in the present invention include, but are not limited to, thymidine kinase-encoding tdk and HSV-tk, thymidylate kinase-encoding tmk, uracil phosphoribosyl transferase-encoding upp or furl, nucleoside diphosphokinase-encoding ndk, etc. Preferably, the cytosine deaminase-encoding gene FCY1 may be used. The name of the gene that encodes cytosine deaminase in yeast is FCY1, and cytosine deaminase-encoding genes having homology thereto are also frequently present in other microorganisms. For example, these genes are coda in E. coli, and FCA1 in Candida albicans.

In the present invention, the range of operation of the synthetic suicide genetic circuit can be regulated by adding an external regulator during culture. When the suicide gene is a cytosine deaminase-encoding gene, the external regulator may be fluorocytosine; and when the suicide gene is a thymidylate kinase- or thymidine kinase-encoding gene, the external regulator may be a pyrimidine nucleoside analog or guanosine analog selected from the group consisting of dideoxythymidine, trifluoromethylthymidine, ethyldeoxyuridine, bromovinyldeoxyuridine, bromovunyl-arabinouracil, and ganciclovir.

Cytosine deaminase that is encoded by the suicide gene FCY1 used in an example of the present invention is an enzyme that removes an amine group from cytosine by hydrolysis to make uracil. When the cytosine analog fluorocytosine is added to cells, cytosine deaminase converts fluorocytosine to fluorouracil by removing an amine group from fluorocytosine. Fluorouracil exhibits toxicity in cells, resulting in dysfunction of RNA, which induces apoptosis (death) of the cells. Thus, fluorocytosine functions as a regulator that regulates the operation of the suicide genetic circuit, and it is possible to regulate the range of operation of the suicide genetic circuit depending on the concentration of fluorocytosine added.

When the suicide gene is a gene other than a cytosine deaminase-encoding gene, an external regulator other than fluorocytosine should be added. For example, when the thymidylate kinase- or thymidine kinase-encoding gene tmk or tkd is used as the suicide gene, one of pyrimidine nucleoside analogs, including dideoxythymidine, trifluoromethylthymidine, ethyldeoxyuridine, bromovinyldeoxyuridine, or bromovunyl-arabinouracil, may be added so that the thymidine moiety thereof can be phosphorylated, thereby inducing cell death. As another example, when the HSV-tk gene is used, the guanosine analog ganciclovir may be added so that it can be converted to a phosphorylated compound, resulting in the termination of DNA synthesis, which induces cell death.

In an example of the present invention, in the case of metabolite-overproducing mutant strains, when the glmS ribozyme did bind to GlcN6P, it cleaved the ORF (open reading frame) of FCY1 so that cytosine deaminase was no longer expressed. Thus, even when fluorocytosine was added, it was not converted to fluorouracil, and thus cell death did not occur. Accordingly, the growth rate of colonies was relatively high, and thus metabolite-overproducing mutant strains could be easily screened. On the other hand, in the case of mutant strains that produce little or no metabolite, cytosine deaminase was expressed due to the absence of the enzymatic action of the glmS ribozyme, and thus when fluorocytosine was added, it was converted to fluorouracil that induced cell death by its toxicity.

In the present invention, the gene that is involved in the production of the target metabolite may be a GFA1-encoding gene that converts fructose-6P to GlcN6P, or a FMN1-encoding gene that converts riboflavin to FMN.

When useful metabolites are to be produced by metabolic engineering, strains are manipulated by two methods: a rational design method and a random screening method. The random screening method has an advantage in that it can be applied even when information about either an accurate pathway for synthesis of a metabolite in the strain of interest or the key procedure of cell growth. Because of this advantage, it has been frequently used in studies on the production of industrially useful metabolites. The random screening method comprises two steps: a step of applying methods, which can make mutants that randomly show different phenotypes, to a certain gene of a strain; and a step of selecting only a strain showing a desired phenotype from among expressed mutants.

In an example of the present invention, in order to produce mutants, which can overproduce GlcN6P, by randomly mutating the glutamine-fructose-6-phosphate transaminase-encoding GFA1 gene (FIG. 1b) that converts the yeast intermediate metabolite fructose-6P to GlcN6P, mutants were produced using error-prone PCR that causes random point mutations, and then these mutants were introduced into a strain (yeast) having a suicide genetic circuit introduced therein, thereby constructing mutant strain libraries. As a result, it could be seen that any mutant strain overproduced GlcN6P so that the suicide genetic circuit was suppressed, and any mutant strain produced little or no GlcN6P so that the suicide genetic circuit operated, suggesting that there was a different in growth rate between the mutant strains.

Likewise, in an example of the present invention, it was found that, even when the suicide gene having introduced therein the FMN ribozyme in place of the glmS ribozyme was introduced into strains, the synthetic suicide gene circuit could operate. Thus, it will be obvious to those skilled in the art that a mutant strain having a fast growth rate can be screened by producing mutants through error-prone PCR for the FMN1-encoding FMN1 gene that converts the yeast intermediate metabolite riboflavin to FMN (flavin mononucleotide), and then introducing the mutants into a strain (yeast) having a suicide genetic circuit introduced therein to thereby construct mutant strain libraries.

In another example of the present invention, mutant strain libraries having introduced therein a synthetic suicide genetic circuit and GFA1 mutants were cultured. As a result, a GFA1-m1 strain having a GFA1 mutant of SEQ ID NO: 2, a GFA-m9 strain having a GFA1 mutant of SEQ ID NO: 3, and a GFA1-m12 strain having a GFA1 mutant of SEQ ID NO: 4, showed the highest growth efficiency, and thus the mutated GFA1 sequences thereof were sequenced. As a result, two conserved mutations (Q96H and Q157R) were observed when compared with the wild-type amino acid sequence of SEQ ID NO: 1.

Thus, in another aspect, the present invention is directed to a GFA1 mutant comprising amino acid mutations of Q96H and Q157R in an amino acid sequence of SEQ ID NO: 1. Preferably, the GFA1 mutant has any one of amino acid sequences of SEQ ID NOs: 2 to 4.

In still another aspect, the present invention is also directed to a GlcN6P-overproducing mutant strain containing a gene that encodes the GFA1 mutant.

In an example of the present invention, each of various HAD phophatase-encoding genes was introduced into the GFA1-m12 strain among the strains having the GFA1 mutant introduced therein, thereby constructing mutant strain libraries. HAD phosphatase is an enzyme that converts GlcNAc6P (N-acetylglucosamine-6-phosphate) to GlcNAc (N-acetylglucosamine) (FIG. 1b), and HAD phosphatase is not present in wild-type yeast, and thus GlcNAc cannot be produced in yeast. However, in the present invention, it could be found that, when a HAD phosphatase-encoding gene was introduced into yeast, the concentration of GlcN6P in the yeast was reduced in the process in which GlcNAc6P was converted to GlcNAc by HAd phosphatase, and thus the suicide genetic circuit operated, suggesting that a GlcNAc-overproducing mutant strain can be screened by selecting a colony having a slow growth rate. The sequence of HAD phosphatase produced in a mutant strain most clearly showing this effect was analyzed, and as a result, it could be seen that the HAD phosphatase is YqaB of SEQ ID NO: 5 or YihX of SEQ ID NO: 6.

Thus, in yet another aspect, the present invention also provides a method for screening a GlcNAc-overproducing mutant strain, the method comprising the steps of: (a) introducing genes encoding various HAD phosphatases into the above-described GlcN6P-overproducing mutant strain to construct mutant strain libraries; (b) culturing each of the mutant strain libraries; and (c) selecting, from among the cultured mutant strains, a mutant strain having a relatively slow growth rate as the GlcNAc-overproducing mutant strain.

In addition, the present invention is directed to a GlcNAc-overproducing mutant strain containing a gene that encodes HAD phosphatase YqaB or YihX.

The growth according to the present invention might mean the rate of growth, for example, could be measured by OD (optical density), which represents the rate of growth in the cultured strain. Having a relatively high growth rate means increase by about more than 10 times, preferably about more than 15 times, more preferably more than 20 times of OD ratio, when compared to the control group. Having a relatively growth rate means decrease by about less than 0.8 times, preferably about less than 0.6 times, more preferably less than 0.4 times of OD ratio, when compared to the control group.

EXAMPLES

Hereinafter, the present invention will be described in further detail with reference to examples. It will be obvious to a person having ordinary skill in the art that these examples are illustrative purposes only and are not to be construed to limit the scope of the present invention.

In the following examples, only the cytosine deaminase-encoding gene FCY1 was illustrated as a suicide gene. However, it will be obvious to those skilled in the art that the cytosine deaminase-encoding gene FCY1 can be replaced with a gene that encodes thymidine kinase, thymidylate kinase, uracil phosphoribosyl transferase, or nucleoside diphosphokinase.

In the following examples, only a glmS or FMN ribozyme was illustrated as a ribozyme inserted into the suicide gene. However, it will be obvious to those skilled in the art that the glmS or FMN ribozyme may be replaced with other ribozymes that can bind to a metabolite to undergo a self-cleavage reaction, for example, ribozymes that bind to at least one effector molecule selected from the group consisting of FMN, ATP, theophylline, tetracyclin, xanthine, TMPyP4, light and caged theophylline, ERK2 phosphorylated/unphosphorylated, HCV helicase/replicase, Tat protein, cAMP, cCMP, cGMP, 3-methylxanthine, caffeine, aspartame, $Mn^{2+}$, $Fe^{2+}$, $Co^{2+}$, $Ni^{2+}$, $Zn^{2+}$, $Cd^{2+}$, Light and (BDHP-COOH or BCPD-COOH).

Example 1: Construction of Suicide Riboswitch to be Introduced into Yeast (*Saccharomyces cerevisiae*) BY4742 Strain 1-1: Construction of Suicide Riboswitch Using glmS Ribozyme First, in order to clone a glmS ribozyme (Nucleic Acids Res. 2006 Feb. 7; 34(3):968-75, "Core requirements for glmS ribozyme self-cleavage reveal a putative pseudoknot structure") using a Klenow fragment (Takara, Shiga, Japan), two DNA primers (GAAATGTAGTTGACGAGGAG/CTCCTCGTCAACTACATTTC) having an overlap of 20 base pairs were added and annealed at room temperature. The annealed primers were incubated together with a Klenow fragment for filling the 3' end. After incubation for 1 hour, the primer complex, containing a glmS ribozyme sequence and filled at the 3' end, was cut with a restriction enzyme and ligated into a plasmid. Using the plasmid having a URA3 cassette following the glmS ribozyme sequence as a template, amplification was performed by a polymerase chain reaction (PCR). In order to introduce the amplified glmS ribozyme gene fragment into a gene in yeast, the gene fragment was amplified by PCR using a primer comprising a 45 bp homology arm (ATTAGAATTCTAATACGACTCACTATAGGTAAATTATAAAAGCGCCAGAACTACAGAAATGTAGTTGACGAGGAG/TAATCTCGAGGGAGGCATCCGCCGAAAATTCGATAAACCTCCTCCTCGTCAACTACATTTC) for homologous recombination.

The gene fragment to be inserted was transformed into *Saccharomyces cerevisiae* BY4742. In order to examine whether the suicide riboswitch was inserted into the gene of the yeast, a colony selected on an SD-URA medium (2% glucose, 0.67% yeast nitrogen base without amino acids, 0.77 g/L CSM-URA dropout mixture) plate was selected. As a result, it could be seen that the glmS ribozyme was inserted into the 3'UTR (untranslated region) of FCY1 locus in the BY4742 strain.

Figure 2:
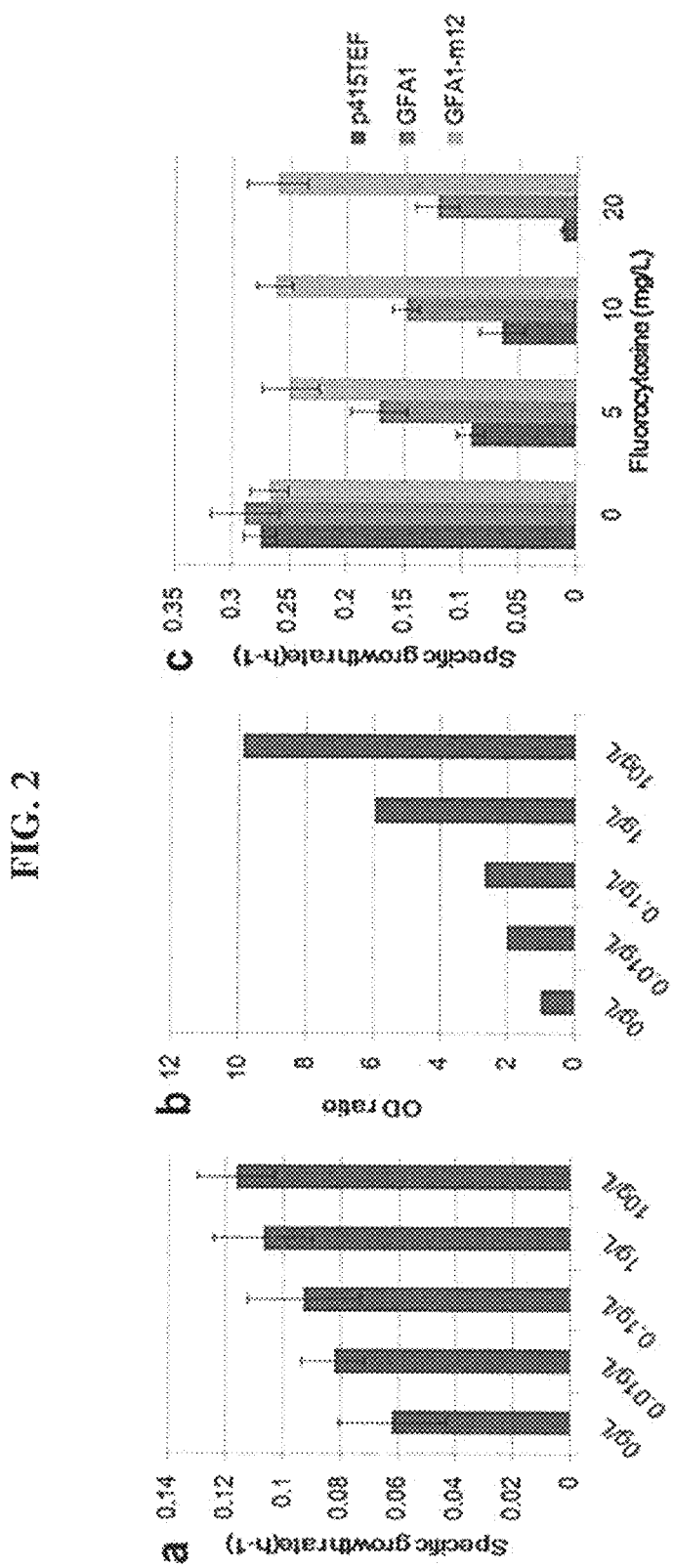
FIG. 2 depicts graphs showing the results of comparing the growth rate of yeast between various concentrations of added GlcN in order to verify the operation of a synthetic suicide genetic circuit containing a glmS ribozyme (FIGS. 2a and 2b), and a graph showing that the range of operation of the suicide circuit can be controlled by adding various concentrations of fluorocytosine (FIG. 2c).

In addition, in order to examine whether the suicide riboswitch operates properly, whether the growth rate of cells having the suicide riboswitch introduced therein changes depending on the concentration of GlcN6P in the cells was examined. In the presence of fluorocytosine, glucosamine (GlcN) was externally added to the culture medium so that it was converted to GlcN6P by intracellular hexokinase. As a result, it could be seen that, as the concentration of GlcN6P increased, the growth rate of the cells increased, because cytosine deaminase was not produced due to the self-cleavage reaction of the glmS ribozyme (FIG. 2a). In addition, it could be seen that the absorbance at 660 nm changed depending on the concentration of GlcN (FIG. 2b).

1-2: Construction of Suicide Riboswitch Using FMN Ribozyme

Using the same method as described in Example 1-1, a FMN ribozyme (Proc. Natl. Acad. Sci. USA Vol. 96, pp. 3584-3589, March 1999, "Engineering precision RNA molecular switches")

Biochemistry was inserted into the 3' UTR of the FCY1 gene (NC_001148.4). In order to examine whether the suicide riboswitch operates properly, an experiment for examining whether the growth rate of cells having the suicide riboswitch introduced therein changes depending on the concentration of FMN in the cells was performed.

Figure 5:
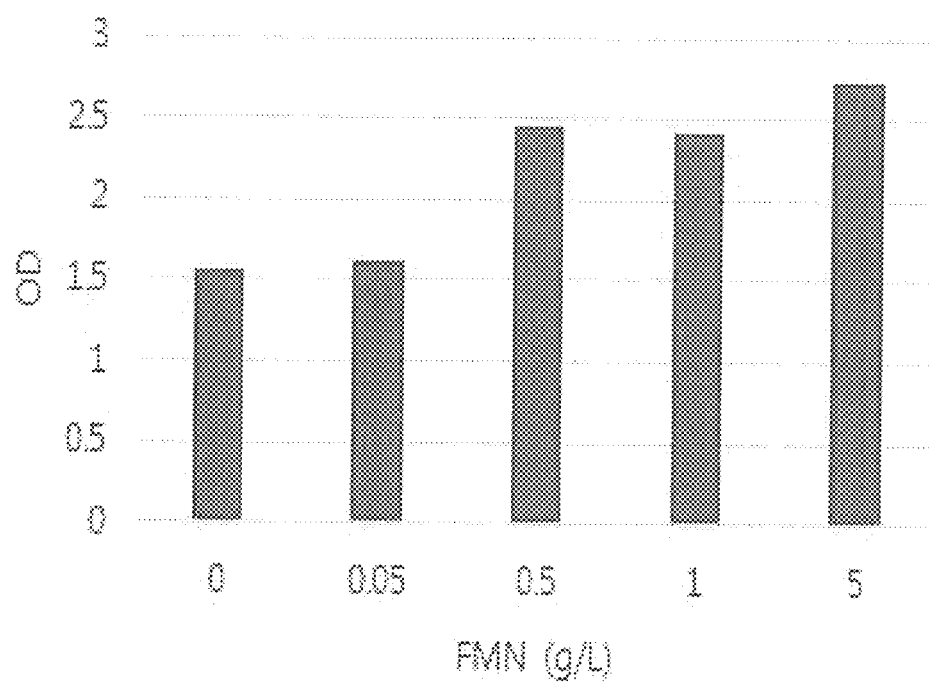
FIG. 5 is a graph showing the results of comparing the growth rate of yeast between various concentrations of added FMN in order to verify the operation of a synthetic suicide genetic circuit containing a FMN ribozyme.

Specifically, FMN was externally added to the culture medium. As a result, it could be seen that, as the concentration of FMN added increased, the growth rate of the enzyme increased and the absorbance also increased, because cytosine deaminase was not produced due to the self-cleavage reaction of the FMN ribozyme (FIG. 5).

In addition, the FMN1 gene was cloned into a p413GPD plasmid, which was then transformed into a strain having the FMN suicide riboswitch introduced therein so that FMN was produced in the cells. Also, the cells were treated with fluorocytosine. As a result, it could be seen that, when FMN was present, the growth rate of the cells was high, because cytosine deaminase was not produced due to the self-cleavage reaction of the FMN ribozyme (FIG. 6b). In addition, it could be seen that the absorbance at 660 nm was high due to the production of FMN (FIG. 6c).

Example 2: Construction of GFA1 Mutant Library and HAD Phosphatase Library

Using error-prone PCR that generates random point mutations, a GFA1 mutant library of yeast (*Saccharomyces cerevisiae*) was produced. Specifically, yeast GFA1 was cloned into a p415TEF plasmid, which was then used as a template for error-prone PCR using a Genemorph II Random Mutagenesis kit (Agilent, CA, USA). The PCR amplification product was ligated into a p415TEF plasmid using Mighty Mix (Takara), and the plasmid was transformed into highly competent *E. coli* DH5α HIT competent cells (RBC, Banqiao City, Taipei County, Taiwan) to maximally recover the plasmid.

23 *E. coli* HAD phosphatases excluding HAD11 were cloned into p413GPD plasmids. For production of a HAD phosphatase library, the plasmids comprising the HAD phosphatase-encoding genes were separated and then mixed together.

Example 3: Construction and Screening of GFA1 Mutant Library and BAD Phosphatase Library Plasmids encoding GFA1 mutants or HAD phosphatases were introduced into a BY4742 FGU (BY4742 containing the glmS suicide riboswitch) strain. Specifically, a BY4742 FGU strains were cultured in YEPD medium (1% yeast extract, 2% peptone, 2% glucose) at 30° C. For transformation, exponentially growing cells were collected by centrifugation at 250 rpm. The GFA1 mutant library was transformed into the BY4742 FGU strain, and the transformants were screened on an SD-LEU-URA medium (2% glucose, 0.67% yeast nitrogen base without amino acids, 0.67 g/L CSM-LEU-URA dropout mixture) plate.

The HAD phosphatase library was transformed into the GFA1-m12 strain showing the highest efficiency, and was screened on an SD-HIS-LEU-URA medium (2% glucose, 0.67% yeast nitrogen base without amino acids, 0.60 g/L CSM-HIS-LEU-URA dropout mixture) plate.

Example 4: Observation of Growth of Mutant Strains Having Suicide Riboswitch Introduced Therein A BY4742 FGU strain and other strains, which have a suicide riboswitch introduced therein, were cultured in minimal media. For culture of BY4742 FGU, SD-URA medium supplemented with 5 mg/L of fluorocytosine was used. At 2 days after seeding, absorbance was used. To screen the GFA1 mutant library, medium supplemented with 10 mg/L of fluorocytosine was used, and to screen the HAD phosphatase library, medium supplemented with 20 mg/L of fluorocytosine was used (FIG. 2c).

Figure 3:
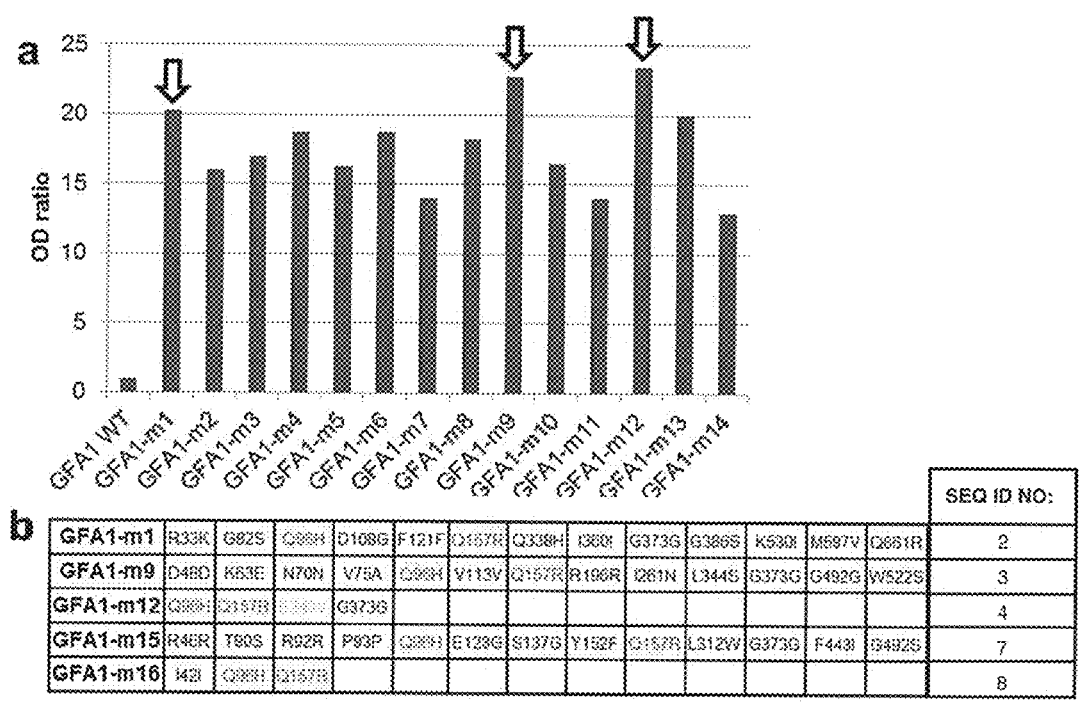
FIG. 3 depicts a graph showing absorbance resulting from the production of a metabolite in various strains introduced with a GFA1 mutant library (FIG. 3a), and the results of analysis performed to examine the positions of mutations in GFA1-m1 (SEQ ID NO: 2), GFA1-m9 (SEQ ID NO: 3) and GFA1-m12 (SEQ ID NO: 4), which showed the highest efficiency (FIG. 3b).

As a result of culturing the strain having the GFA1 mutant library introduced therein, 14 colonies were separated according to size, and the state of growth was compared between the colonies. The results of measurement of absorbance by using UV-vis spectrophotometer (SHIMADZU UV mini 1240) showed that GFA1-m1 (SEQ ID NO: 2), GFA-m9 (SEQ ID NO: 3) and GFA1-m12 (SEQ ID NO: 4) strains produced GlcN6P in the largest amount, suggesting that these strains showed the highest growth rate (FIG. 3a) and the absorbance of the mutant strains was increased by more than about 20 times when compared to the control group strains. The mutated GFA1 sequences of these strains were analyzed (FIG. 3b). As a result, two conserved mutations (Q96H and Q157R) were observed commonly in the three strains. In addition, the two conserved mutations (Q96H and Q157R) were also observed in the cultured GFA1-m15 (SEQ ID NO: 7) and GFA1-m16 (SEQ ID NO: 8) (FIG. 3b).

Figure 4:
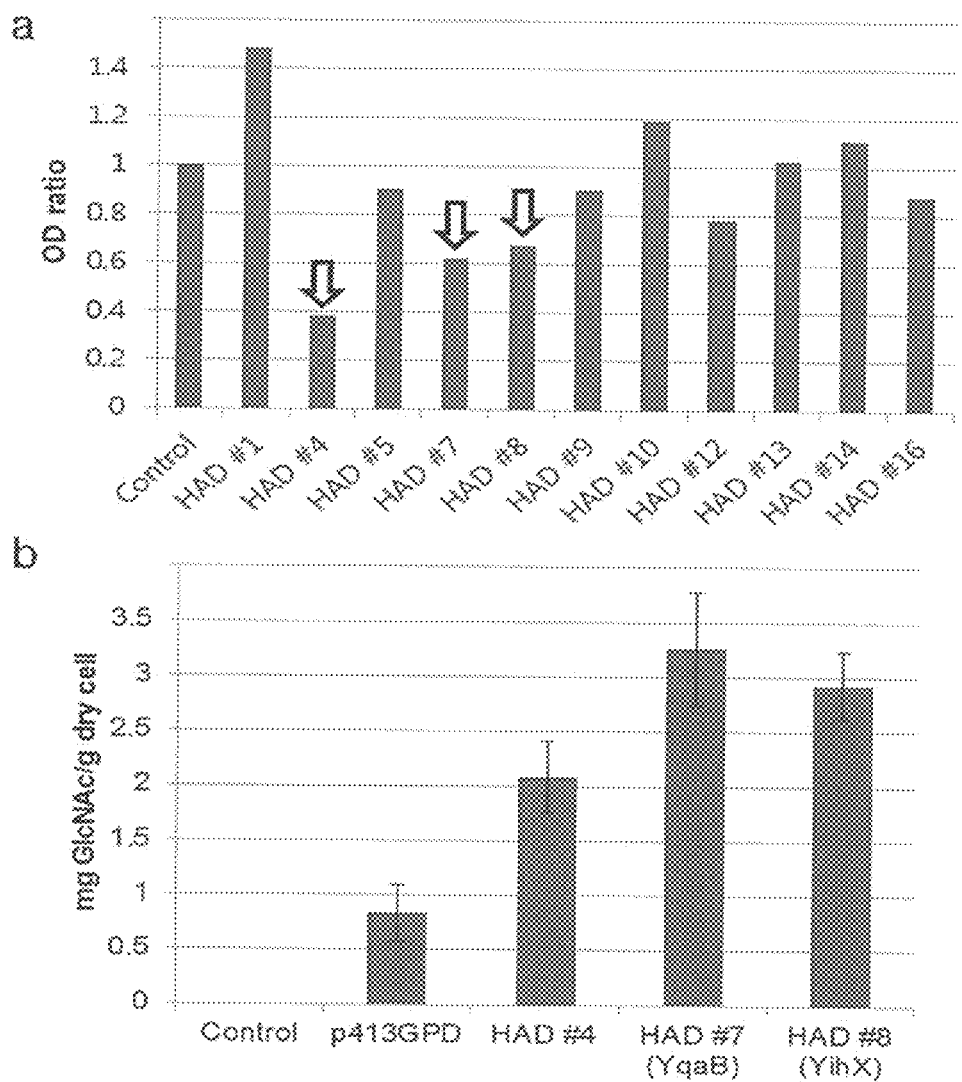
FIG. 4 depicts a graph showing absorbance resulting from the production of a metabolite when a HAD phosphatase library was introduced into a GFA1-m12 strain showing the highest efficiency (FIG. 4a), and a graph showing that GlcNAc can be produced in yeast that could not produce GlcNAc, when the HAD phosphatase library is introduced into the yeast (FIG. 4b).

Also, for the GFA1-m12 strain having the HAD phosphatase library introduced therein, a total of 12 colonies were isolated, and the absorbance thereof was measured. As a result, it could be seen that HAD #4, HAD #6, HAD #7 and HAD #8 showed reduced absorbance, suggesting that the production of GlcN6P therein was reduced (FIG. 4a). The absorbance of the mutant strains was decreased by less than about 0.8 times when compared to the control group strains.

In addition, whether these strains produce GlcNAc was analyzed. As a result, it could be seen that BY4742 FGU having no HAD phosphatase introduced therein produced no GlcNAc, whereas the production of GlcNAc in HAD #7 and HAD #8 increased. The sequences of HAD phosphatases produced in HAD #7 and HAD #8 were analyzed, and as a result, it could be seen that YqaB (SEQ ID NO: 5) and YihX (SEQ ID NO: 6) were introduced in the HAD phosphatases, respectively (FIG. 4d).

Example 5: Measurement of Concentration of GlcNAc by HPLC (High-Performance Liquid Chromatography)

The measurement of GlcNAc in Example 4 was measured by HPLC (high-performance liquid chromatography). GlcNAc in cells was extracted with boiling ethanol, and concentrated using a speed vacuum concentrator (Hanil, Incheon, Korea). The concentrated intracellular metabolite was dissolved in water and analyzed by HPLC (YL instrument, Anyang, Korea). The concentration of GlcNAc was analyzed using 10 mM $H_2SO_4$ solution as an eluent, an RI detector and a Shodex SUGAR SH1011 column (8.0 mm×300 mm).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for screening a target metabolite-overproducing mutant strain, the method comprising the steps of:
    (a) constructing mutant strain libraries that have introduced therein a synthetic suicide genetic circuit comprising a suicide gene and a riboswitch, and the mutant strain libraries comprising mutants of a gene that is involved in the production of the target metabolite;
    (b) culturing each of the mutant strain libraries; and
    (c) selecting, from among the cultured mutant strain libraries, a mutant strain having a faster growth rate than wild-type strain as the target metabolite-overproducing mutant strain,
    wherein in the mutant strain that overproduces the target metabolite, the overproduced target metabolite binds to the riboswitch to suppress the operation of synthetic suicide genetic circuit, and in a mutant strain that produces little or no target metabolite, the synthetic suicide genetic circuit operates to induce the death of the mutant strain, and
    wherein the riboswitch is a ribozyme that cleaves the suicide gene by enzymatic action after binding to the target metabolite and the ribozyme is either a glmS ribozyme that binds to GlcN6P, or a ribozyme that binds to at least one effector molecule selected from the group consisting of FMN, ATP, theophylline, tetracyclin, xanthine, 3-methylxanthine and caffeine, and
    wherein the suicide gene is selected from the group consisting of cytosine deaminase-, thymidine kinase-, thymidylate kinase-, uracil phosphoribosyl transferase- and nucleoside diphosphokinase-encoding genes.

2. The method of claim 1, wherein the mutant strain libraries are constructed using bacteria or yeast.

3. The method of claim 1, wherein the riboswitch is inserted into the 3' UTR (untranslated region) of pre-mRNA of the suicide gene.

4. The method of claim 1, wherein a range of operation of the synthetic suicide genetic circuit is regulated by adding an external regulator during culture.

5. The method of claim 4, wherein the external regulator is fluorocytosine, provided that the suicide gene is a cytosine deaminase-encoding gene; and the external regulator is a pyrimidine nucleoside analog or guanosine analog selected from the group consisting of dideoxythymidine, trifluoromethylthymidine, ethyldeoxyuridine, bromovinyldeoxyuridine, bromovunyl-arabinouracil, and ganciclovir, provided that the suicide gene is a thymidylate kinase- or thymidine kinase-encoding gene.

6. The method of claim 1, wherein the gene that is involved in the production of the target metabolite is a GFA1-encoding gene that converts fructose-6P to GlcN6P, or a FMN1-encoding gene that converts riboflavin to FMN.

7. The method of claim 1, wherein the mutants of a gene that is involved in the production of the target metabolite is a GFA1 mutant comprising amino acid mutations of Q96H and Q157R in an amino acid sequence of SEQ ID NO: 1.

8. The method of claim 1, wherein the mutants of a gene that is involved in the production of the target metabolite comprise a mutant represented by any one of amino acid sequences of SEQ ID NOs: 2 to 4.

* * * * *

UNITED STATES PATENT AND TRADEMARK OFFICE
CERTIFICATE OF CORRECTION

PATENT NO.         : 9,963,696 B2
APPLICATION NO.    : 14/515408
DATED              : May 8, 2018
INVENTOR(S)        : Min-Kyu Oh

It is certified that error appears in the above-identified patent and that said Letters Patent is hereby corrected as shown below:

In the Specification

Column 5, Line 55: "PreQi" should be -- PreQ1 --.

Column 11, Line 2: "BAD" should be -- HAD --.

Signed and Sealed this
Nineteenth Day of June, 2018

Andrei Iancu
*Director of the United States Patent and Trademark Office*

SEQUENCE LISTING

```
<160> NUMBER OF SEQ ID NOS: 8

<210> SEQ ID NO 1
<211> LENGTH: 717
<212> TYPE: PRT
<213> ORGANISM: Artificial Sequence
<220> FEATURE:
<223> OTHER INFORMATION: GFA1 from Saccharomyces cerevisiae

<400> SEQUENCE: 1
```

Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Asp Glu Ala Asp
        35                  40                  45

Ser Thr Phe Ile Tyr Lys Gln Ile Gly Lys Val Ser Ala Leu Lys Glu

```
                50                  55                  60
Glu Ile Thr Lys Gln Asn Pro Asn Arg Asp Val Thr Phe Val Ser His
 65                  70                  75                  80

Cys Gly Ile Ala His Thr Arg Trp Ala Thr His Gly Arg Pro Glu Gln
                 85                  90                  95

Val Asn Cys His Pro Gln Arg Ser Asp Pro Glu Asp Gln Phe Val Val
                100                 105                 110

Val His Asn Gly Ile Ile Thr Asn Phe Arg Glu Leu Lys Thr Leu Leu
                115                 120                 125

Ile Asn Lys Gly Tyr Lys Phe Glu Ser Asp Thr Asp Thr Glu Cys Ile
130                 135                 140

Ala Lys Leu Tyr Leu His Leu Tyr Asn Thr Asn Leu Gln Asn Gly His
145                 150                 155                 160

Asp Leu Asp Phe His Glu Leu Thr Lys Leu Val Leu Glu Leu Glu
                165                 170                 175

Gly Ser Tyr Gly Leu Leu Cys Lys Ser Cys His Tyr Pro Asn Glu Val
                180                 185                 190

Ile Ala Thr Arg Lys Gly Ser Pro Leu Leu Ile Gly Val Lys Ser Glu
                195                 200                 205

Lys Lys Leu Lys Val Asp Phe Val Asp Val Glu Phe Pro Glu Glu Asn
                210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Ile Ala Ala Asn Glu Phe Asn Leu Arg His Ser Gln
                260                 265                 270

Ser Arg Ala Phe Leu Ser Glu Asp Gly Ser Pro Thr Pro Val Glu Phe
                275                 280                 285

Phe Val Ser Ser Asp Ala Ala Ser Val Val Lys His Thr Lys Lys Val
                290                 295                 300

Leu Phe Leu Glu Asp Asp Asp Leu Ala His Ile Tyr Asp Gly Glu Leu
305                 310                 315                 320

His Ile His Arg Ser Arg Arg Glu Val Gly Ala Ser Met Thr Arg Ser
                325                 330                 335

Ile Gln Thr Leu Glu Met Glu Leu Ala Gln Ile Met Lys Gly Pro Tyr
                340                 345                 350

Asp His Phe Met Gln Lys Glu Ile Tyr Glu Gln Pro Glu Ser Thr Phe
                355                 360                 365

Asn Thr Met Arg Gly Arg Ile Asp Tyr Glu Asn Asn Lys Val Ile Leu
                370                 375                 380

Gly Gly Leu Lys Ala Trp Leu Pro Val Val Arg Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
                420                 425                 430

Ser Asp Phe Leu Asp Arg Lys Cys Pro Val Phe Arg Asp Asp Val Cys
                435                 440                 445

Val Phe Val Ser Gln Ser Gly Glu Thr Ala Asp Thr Met Leu Ala Leu
                450                 455                 460

Asn Tyr Cys Leu Glu Arg Gly Ala Leu Thr Val Gly Ile Val Asn Ser
465                 470                 475                 480
```

```
Val Gly Ser Ser Ile Ser Arg Val Thr His Cys Val His Ile Asn
            485                 490                 495

Ala Gly Pro Glu Ile Gly Val Ala Ser Thr Lys Ala Tyr Thr Ser Gln
        500                 505                 510

Tyr Ile Ala Leu Val Met Phe Ala Leu Ser Leu Ser Asp Asp Arg Val
            515                 520                 525

Ser Lys Ile Asp Arg Arg Ile Glu Ile Ile Gln Gly Leu Lys Leu Ile
        530                 535                 540

Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Leu Gly
            565                 570                 575

Arg Gly Tyr Gln Phe Ala Ala Ala Leu Glu Gly Ala Leu Lys Ile Lys
        580                 585                 590

Glu Ile Ser Tyr Met His Ser Glu Gly Val Leu Ala Gly Glu Leu Lys
            595                 600                 605

His Gly Val Leu Ala Leu Val Asp Glu Asn Leu Pro Ile Ile Ala Phe
        610                 615                 620

Gly Thr Arg Asp Ser Leu Phe Pro Lys Val Val Ser Ser Ile Glu Gln
625                 630                 635                 640

Val Thr Ala Arg Lys Gly His Pro Ile Ile Ile Cys Asn Glu Asn Asp
            645                 650                 655

Glu Val Trp Ala Gln Lys Ser Lys Ser Ile Asp Leu Gln Thr Leu Glu
        660                 665                 670

Val Pro Gln Thr Val Asp Cys Leu Gln Gly Leu Ile Asn Ile Ile Pro
            675                 680                 685

Leu Gln Leu Met Ser Tyr Trp Leu Ala Val Asn Lys Gly Ile Asp Val
        690                 695                 700

Asp Phe Pro Arg Asn Leu Ala Lys Ser Val Thr Val Glu
705                 710                 715

<210> SEQ ID NO 2
<211> LENGTH: 717
<212> TYPE: PRT
<213> ORGANISM: Artificial Sequence
<220> FEATURE:
<223> OTHER INFORMATION: GFA1-m1

<400> SEQUENCE: 2

Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Lys Gly Tyr Asp Ser Thr Gly Ile Ala Ile Asp Gly Glu Ala Asp
        35                  40                  45

Ser Thr Phe Ile Tyr Lys Gln Ile Gly Lys Val Ser Ala Leu Lys Glu
    50                  55                  60

Glu Ile Thr Lys Gln Asn Pro Asn Arg Asp Val Thr Phe Val Ser His
65                  70                  75                  80

Cys Ser Ile Ala His Thr Arg Trp Ala Thr His Gly Arg Pro Glu His
            85                  90                  95

Val Asn Cys His Pro Gln Arg Ser Asp Pro Glu Gly Gln Phe Val Val
        100                 105                 110

Val His Asn Gly Ile Ile Thr Asn Phe Arg Glu Leu Lys Thr Leu Leu
    115                 120                 125
```

```
Ile Asn Lys Gly Tyr Lys Phe Glu Ser Asp Thr Asp Thr Glu Cys Ile
130                 135                 140

Ala Lys Leu Tyr Leu His Leu Tyr Asn Thr Asn Leu Arg Asn Gly His
145                 150                 155                 160

Asp Leu Asp Phe His Glu Leu Thr Lys Leu Val Leu Leu Glu Leu Glu
                165                 170                 175

Gly Ser Tyr Gly Leu Leu Cys Lys Ser Cys His Tyr Pro Asn Glu Val
                180                 185                 190

Ile Ala Thr Arg Lys Gly Ser Pro Leu Leu Ile Gly Val Lys Ser Glu
                195                 200                 205

Lys Lys Leu Lys Val Asp Phe Val Asp Val Glu Phe Pro Glu Glu Asn
210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Ile Ala Ala Asn Glu Phe Asn Leu Arg His Ser Gln
                260                 265                 270

Ser Arg Ala Phe Leu Ser Glu Asp Gly Ser Pro Thr Pro Val Glu Phe
            275                 280                 285

Phe Val Ser Ser Asp Ala Ala Ser Val Val Lys His Thr Lys Lys Val
290                 295                 300

Leu Phe Leu Glu Asp Asp Leu Ala His Ile Tyr Asp Gly Glu Leu
305                 310                 315                 320

His Ile His Arg Ser Arg Arg Glu Val Gly Ala Ser Met Thr Arg Ser
                325                 330                 335

Ile His Thr Leu Glu Met Glu Leu Ala Gln Ile Met Lys Gly Pro Tyr
                340                 345                 350

Asp His Phe Met Gln Lys Glu Ile Tyr Glu Gln Pro Glu Ser Thr Phe
            355                 360                 365

Asn Thr Met Arg Gly Arg Ile Asp Tyr Glu Asn Asn Lys Val Ile Leu
            370                 375                 380

Gly Ser Leu Lys Ala Trp Leu Pro Val Val Arg Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
                420                 425                 430

Ser Asp Phe Leu Asp Arg Lys Cys Pro Val Phe Arg Asp Asp Val Cys
            435                 440                 445

Val Phe Val Ser Gln Ser Gly Glu Thr Ala Asp Thr Met Leu Ala Leu
450                 455                 460

Asn Tyr Cys Leu Glu Arg Gly Ala Leu Thr Val Gly Ile Val Asn Ser
465                 470                 475                 480

Val Gly Ser Ser Ile Ser Arg Val Thr His Cys Gly Val His Ile Asn
                485                 490                 495

Ala Gly Pro Glu Ile Gly Val Ala Ser Thr Lys Ala Tyr Thr Ser Gln
            500                 505                 510

Tyr Ile Ala Leu Val Met Phe Ala Leu Ser Leu Ser Asp Asp Arg Val
            515                 520                 525

Ser Ile Ile Asp Arg Arg Ile Glu Ile Ile Gln Gly Leu Lys Leu Ile
530                 535                 540
```

```
Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Leu Gly
                565                 570                 575

Arg Gly Tyr Gln Phe Ala Ala Ala Leu Glu Gly Ala Leu Lys Ile Lys
            580                 585                 590

Glu Ile Ser Tyr Val His Ser Glu Gly Val Leu Ala Gly Glu Leu Lys
        595                 600                 605

His Gly Val Leu Ala Leu Val Asp Glu Asn Leu Pro Ile Ile Ala Phe
    610                 615                 620

Gly Thr Arg Asp Ser Leu Phe Pro Lys Val Val Ser Ser Ile Glu Gln
625                 630                 635                 640

Val Thr Ala Arg Lys Gly His Pro Ile Ile Cys Asn Glu Asn Asp
                645                 650                 655

Glu Val Trp Ala Arg Lys Ser Lys Ser Ile Asp Leu Gln Thr Leu Glu
                660                 665                 670

Val Pro Gln Thr Val Asp Cys Leu Gln Gly Leu Ile Asn Ile Pro
            675                 680                 685

Leu Gln Leu Met Ser Tyr Trp Leu Ala Val Asn Lys Gly Ile Asp Val
690                 695                 700

Asp Phe Pro Arg Asn Leu Ala Lys Ser Val Thr Val Glu
705                 710                 715

<210> SEQ ID NO 3
<211> LENGTH: 717
<212> TYPE: PRT
<213> ORGANISM: Artificial Sequence
<220> FEATURE:
<223> OTHER INFORMATION: GFA1-m9

<400> SEQUENCE: 3

Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
                20                  25                  30

Arg Gly Tyr Asp Ser Thr Gly Ile Ala Ile Asp Gly Asp Glu Ala Asp
            35                  40                  45

Ser Thr Phe Ile Tyr Lys Gln Ile Gly Lys Val Ser Ala Leu Glu Glu
        50                  55                  60

Glu Ile Thr Lys Gln Asn Pro Asn Arg Asp Ala Thr Phe Val Ser His
65                  70                  75                  80

Cys Gly Ile Ala His Thr Arg Trp Ala Thr His Gly Arg Pro Glu His
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
130                 135                 140

Ala Lys Leu Tyr Leu His Leu Tyr Asn Thr Asn Leu Arg Asn Gly His
145                 150                 155                 160

Asp Leu Asp Phe His Glu Leu Thr Lys Leu Val Leu Glu Leu Glu
                165                 170                 175

Gly Ser Tyr Gly Leu Leu Cys Lys Ser Cys His Tyr Pro Asn Glu Val
            180                 185                 190
```

```
Ile Ala Thr Arg Lys Gly Ser Pro Leu Leu Ile Gly Val Lys Ser Glu
            195                 200                 205
Lys Lys Leu Lys Val Asp Phe Val Asp Val Glu Phe Pro Glu Glu Asn
210                 215                 220
Ala Gly Gln Pro Glu Ile Pro Leu Lys Ser Asn Asn Lys Ser Phe Gly
225                 230                 235                 240
Leu Gly Pro Lys Lys Ala Arg Glu Phe Glu Ala Gly Ser Gln Asn Ala
            245                 250                 255
Asn Leu Leu Pro Asn Ala Ala Asn Glu Phe Asn Leu Arg His Ser Gln
            260                 265                 270
Ser Arg Ala Phe Leu Ser Glu Asp Gly Ser Pro Thr Pro Val Glu Phe
            275                 280                 285
Phe Val Ser Ser Asp Ala Ala Ser Val Val Lys His Thr Lys Lys Val
            290                 295                 300
Leu Phe Leu Glu Asp Asp Leu Ala His Ile Tyr Asp Gly Glu Leu
305                 310                 315                 320
His Ile His Arg Ser Arg Arg Glu Val Gly Ala Ser Met Thr Arg Ser
                325                 330                 335
Ile Gln Thr Leu Glu Met Glu Ser Ala Gln Ile Met Lys Gly Pro Tyr
            340                 345                 350
Asp His Phe Met Gln Lys Glu Ile Tyr Glu Gln Pro Glu Ser Thr Phe
            355                 360                 365
Asn Thr Met Arg Gly Arg Ile Asp Tyr Glu Asn Asn Lys Val Ile Leu
            370                 375                 380
Gly Gly Leu Lys Ala Trp Leu Pro Val Val Arg Arg Ala Arg Arg Leu
385                 390                 395                 400
Ile Met Ile Ala Cys Gly Thr Ser Tyr His Ser Cys Leu Ala Thr Arg
                405                 410                 415
Ala Ile Phe Glu Glu Leu Ser Asp Ile Pro Val Ser Val Glu Leu Ala
            420                 425                 430
Ser Asp Phe Leu Asp Arg Lys Cys Pro Val Phe Arg Asp Asp Val Cys
            435                 440                 445
Val Phe Val Ser Gln Ser Gly Glu Thr Ala Asp Thr Met Leu Ala Leu
450                 455                 460
Asn Tyr Cys Leu Glu Arg Gly Ala Leu Thr Val Gly Ile Val Asn Ser
465                 470                 475                 480
Val Gly Ser Ser Ile Ser Arg Val Thr His Cys Gly Val His Ile Asn
                485                 490                 495
Ala Gly Pro Glu Ile Gly Val Ala Ser Thr Lys Ala Tyr Thr Ser Gln
            500                 505                 510
Tyr Ile Ala Leu Val Met Phe Ala Leu Ser Leu Ser Asp Asp Arg Val
            515                 520                 525
Ser Lys Ile Asp Arg Arg Ile Glu Ile Ile Gln Gly Leu Lys Leu Ile
530                 535                 540
Pro Gly Gln Ile Lys Gln Val Leu Lys Leu Glu Pro Arg Ile Lys Lys
545                 550                 555                 560
Leu Cys Ala Thr Glu Leu Lys Asp Gln Lys Ser Leu Leu Leu Leu Gly
                565                 570                 575
Arg Gly Tyr Gln Phe Ala Ala Ala Leu Glu Gly Ala Leu Lys Ile Lys
            580                 585                 590
Glu Ile Ser Tyr Met His Ser Glu Gly Val Leu Ala Gly Glu Leu Lys
            595                 600                 605
His Gly Val Leu Ala Leu Val Asp Glu Asn Leu Pro Ile Ile Ala Phe
```

-continued

```
                610                 615                 620
Gly Thr Arg Asp Ser Leu Phe Pro Lys Val Val Ser Ile Glu Gln
625                 630                 635                 640

Val Thr Ala Arg Lys Gly His Pro Ile Ile Ile Cys Asn Glu Asn Asp
                    645                 650                 655

Glu Val Trp Ala Gln Lys Ser Lys Ser Ile Asp Leu Gln Thr Leu Glu
                    660                 665                 670

Val Pro Gln Thr Val Asp Cys Leu Gln Gly Leu Ile Asn Ile Pro
            675                 680                 685

Leu Gln Leu Met Ser Tyr Trp Leu Ala Val Asn Lys Gly Ile Asp Val
            690                 695                 700

Asp Phe Pro Arg Asn Leu Ala Lys Ser Val Thr Val Glu
705                 710                 715
```

<210> SEQ ID NO 4
<211> LENGTH: 717
<212> TYPE: PRT
<213> ORGANISM: Artificial Sequence
<220> FEATURE:
<223> OTHER INFORMATION: GFA1-m12

<400> SEQUENCE: 4

```
Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
                20                  25                  30

Arg Gly Tyr Asp Ser Thr Gly Ile Ala Ile Asp Gly Asp Glu Ala Asp
            35                  40                  45

Ser Thr Phe Ile Tyr Lys Gln Ile Gly Lys Val Ser Ala Leu Lys Glu
50                  55                  60

Glu Ile Thr Lys Gln Asn Pro Asn Arg Asp Val Thr Phe Val Ser His
65                  70                  75                  80

Cys Gly Ile Ala His Thr Arg Trp Ala Thr His Gly Arg Pro Glu His
                85                  90                  95

Val Asn Cys His Pro Gln Arg Ser Asp Pro Glu Asp Gln Phe Val Val
                100                 105                 110

Val His Asn Gly Ile Ile Thr Asn Phe Arg Glu Leu Lys Thr Leu Leu
            115                 120                 125

Ile Asn Lys Gly Tyr Lys Phe Glu Ser Asp Thr Asp Thr Glu Cys Ile
130                 135                 140

Ala Lys Leu Tyr Leu His Leu Tyr Asn Thr Asn Leu Arg Asn Gly His
145                 150                 155                 160

Asp Leu Asp Phe His Glu Leu Thr Lys Leu Val Leu Glu Leu Glu
                165                 170                 175

Gly Ser Tyr Gly Leu Leu Cys Lys Ser Cys His Tyr Pro Asn Glu Val
                180                 185                 190

Ile Ala Thr Arg Lys Gly Ser Pro Leu Leu Ile Gly Val Lys Ser Glu
            195                 200                 205

Lys Lys Leu Lys Val Asp Phe Val Asp Val Glu Phe Pro Glu Glu Asn
210                 215                 220

Ala Gly Gln Pro Glu Ile Pro Leu Lys Ser Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Ile Ala Ala Asn Glu Phe Asn Leu Arg His Ser Gln
```

-continued

```
                260                 265                 270
Ser Arg Ala Phe Leu Ser Glu Asp Gly Ser Pro Thr Pro Val Glu Phe
            275                 280                 285
Phe Val Ser Ser Asp Ala Ala Ser Val Val Lys His Thr Lys Lys Val
        290                 295                 300
Leu Phe Leu Glu Asp Asp Leu Ala His Ile Tyr Asp Gly Glu Leu
305                 310                 315                 320
His Ile His Arg Ser Arg Arg Glu Val Gly Ala Ser Met Thr Arg Ser
                325                 330                 335
Ile Gln Thr Leu Glu Met Val Leu Ala Gln Ile Met Lys Gly Pro Tyr
            340                 345                 350
Asp His Phe Met Gln Lys Glu Ile Tyr Glu Gln Pro Glu Ser Thr Phe
        355                 360                 365
Asn Thr Met Arg Gly Arg Ile Asp Tyr Glu Asn Asn Lys Val Ile Leu
    370                 375                 380
Gly Gly Leu Lys Ala Trp Leu Pro Val Val Arg Arg Ala Arg Arg Leu
385                 390                 395                 400
Ile Met Ile Ala Cys Gly Thr Ser Tyr His Ser Cys Leu Ala Thr Arg
                405                 410                 415
Ala Ile Phe Glu Glu Leu Ser Asp Ile Pro Val Ser Val Glu Leu Ala
            420                 425                 430
Ser Asp Phe Leu Asp Arg Lys Cys Pro Val Phe Arg Asp Asp Val Cys
        435                 440                 445
Val Phe Val Ser Gln Ser Gly Glu Thr Ala Asp Thr Met Leu Ala Leu
    450                 455                 460
Asn Tyr Cys Leu Glu Arg Gly Ala Leu Thr Val Gly Ile Val Asn Ser
465                 470                 475                 480
Val Gly Ser Ser Ile Ser Arg Val Thr His Cys Gly Val His Ile Asn
                485                 490                 495
Ala Gly Pro Glu Ile Gly Val Ala Ser Thr Lys Ala Tyr Thr Ser Gln
            500                 505                 510
Tyr Ile Ala Leu Val Met Phe Ala Leu Ser Leu Ser Asp Asp Arg Val
        515                 520                 525
Ser Lys Ile Asp Arg Arg Ile Glu Ile Ile Gln Gly Leu Lys Leu Ile
    530                 535                 540
Pro Gly Gln Ile Lys Gln Val Leu Lys Leu Glu Pro Arg Ile Lys Lys
545                 550                 555                 560
Leu Cys Ala Thr Glu Leu Lys Asp Gln Lys Ser Leu Leu Leu Gly
                565                 570                 575
Arg Gly Tyr Gln Phe Ala Ala Ala Leu Glu Gly Ala Leu Lys Ile Lys
            580                 585                 590
Glu Ile Ser Tyr Met His Ser Glu Gly Val Leu Ala Gly Glu Leu Lys
        595                 600                 605
His Gly Val Leu Ala Leu Val Asp Glu Asn Leu Pro Ile Ile Ala Phe
    610                 615                 620
Gly Thr Arg Asp Ser Leu Phe Pro Lys Val Val Ser Ser Ile Glu Gln
625                 630                 635                 640
Val Thr Ala Arg Lys Gly His Pro Ile Ile Ile Cys Asn Glu Asn Asp
                645                 650                 655
Glu Val Trp Ala Gln Lys Ser Lys Ser Ile Asp Leu Gln Thr Leu Glu
            660                 665                 670
Val Pro Gln Thr Val Asp Cys Leu Gln Gly Leu Ile Asn Ile Ile Pro
        675                 680                 685
```

```
Leu Gln Leu Met Ser Tyr Trp Leu Ala Val Asn Lys Gly Ile Asp Val
        690                 695                 700

Asp Phe Pro Arg Asn Leu Ala Lys Ser Val Thr Val Glu
705                 710                 715

<210> SEQ ID NO 5
<211> LENGTH: 188
<212> TYPE: PRT
<213> ORGANISM: Artificial Sequence
<220> FEATURE:
<223> OTHER INFORMATION: HAD phosphatase YqaB

<400> SEQUENCE: 5

Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
            20                  25                  30

His Tyr Gly Leu Gln Tyr Asp Ile Gln Ala Met Ile Ala Leu Asn Gly
        35                  40                  45

Ser Pro Thr Trp Arg Ile Ala Gln Ala Ile Ile Glu Leu Asn Gln Ala
    50                  55                  60

Asp Leu Asp Pro His Ala Leu Ala Arg Glu Lys Thr Glu Ala Val Arg
65                  70                  75                  80

Ser Met Leu Leu Asp Ser Val Glu Pro Leu Pro Leu Val Asp Val Val
                85                  90                  95

Lys Ser Trp His Gly Arg Arg Pro Met Ala Val Gly Thr Gly Ser Glu
            100                 105                 110

Ser Ala Ile Ala Glu Ala Leu Leu Ala His Leu Gly Leu Arg His Tyr
        115                 120                 125

Phe Asp Ala Val Val Ala Asp His Val Lys His His Lys Pro Ala
    130                 135                 140

Pro Asp Thr Phe Leu Leu Cys Ala Gln Arg Met Gly Val Gln Pro Thr
145                 150                 155                 160

Gln Cys Val Val Phe Glu Asp Ala Asp Phe Gly Ile Gln Ala Ala Arg
                165                 170                 175

Ala Ala Gly Met Asp Ala Val Asp Val Arg Leu Leu
            180                 185

<210> SEQ ID NO 6
<211> LENGTH: 199
<212> TYPE: PRT
<213> ORGANISM: Artificial Sequence
<220> FEATURE:
<223> OTHER INFORMATION: HAD phosphatase YihX

<400> SEQUENCE: 6

Met Leu Tyr Ile Phe Asp Leu Gly Asn Val Ile Val Asp Ile Asp Phe
1               5                   10                  15

Asn Arg Val Leu Gly Ala Trp Ser Asp Leu Thr Arg Ile Pro Leu Ala
            20                  25                  30

Ser Leu Lys Lys Ser Phe His Met Gly Glu Ala Phe His Gln His Glu
        35                  40                  45

Arg Gly Glu Ile Ser Asp Glu Ala Phe Ala Glu Ala Leu Cys His Glu
    50                  55                  60

Met Ala Leu Pro Leu Ser Tyr Glu Gln Phe Ser His Gly Trp Gln Ala
65                  70                  75                  80

Val Phe Val Ala Leu Arg Pro Glu Val Ile Ala Ile Met His Lys Leu
```

```
                85                  90                  95
Arg Glu Gln Gly His Arg Val Val Leu Ser Asn Thr Asn Arg Leu
            100                 105                 110

His Thr Thr Phe Trp Pro Glu Glu Tyr Pro Glu Ile Arg Asp Ala Ala
            115                 120                 125

Asp His Ile Tyr Leu Ser Gln Asp Leu Gly Met Arg Lys Pro Glu Ala
            130                 135                 140

Arg Ile Tyr Gln His Val Leu Gln Ala Glu Gly Phe Ser Pro Ser Asp
145                 150                 155                 160

Thr Val Phe Phe Asp Asp Asn Ala Asp Asn Ile Glu Gly Ala Asn Gln
            165                 170                 175

Leu Gly Ile Thr Ser Ile Leu Val Lys Asp Lys Thr Thr Ile Pro Asp
            180                 185                 190

Tyr Phe Ala Lys Val Leu Cys
            195

<210> SEQ ID NO 7
<211> LENGTH: 717
<212> TYPE: PRT
<213> ORGANISM: Artificial Sequence
<220> FEATURE:
<223> OTHER INFORMATION: GFA-m15 mutant from Saccharomyces cerevisiae

<400> SEQUENCE: 7

Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Asp Glu Ala Asp
            35                  40                  45

Ser Thr Phe Ile Tyr Lys Gln Ile Gly Lys Val Ser Ala Leu Lys Glu
    50                  55                  60

Glu Ile Thr Lys Gln Asn Pro Asn Arg Asp Val Thr Phe Val Ser His
65                  70                  75                  80

Cys Gly Ile Ala His Thr Arg Trp Ala Ser His Gly Arg Pro Glu His
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Gly Leu Lys Thr Leu Leu
            115                 120                 125

Ile Asn Lys Gly Tyr Lys Phe Glu Gly Asp Thr Asp Thr Glu Cys Ile
            130                 135                 140

Ala Lys Leu Tyr Leu His Leu Phe Asn Thr Asn Leu Arg Asn Gly His
145                 150                 155                 160

Asp Leu Asp Phe His Glu Leu Thr Lys Leu Val Leu Glu Leu Glu
            165                 170                 175

Gly Ser Tyr Gly Leu Leu Cys Lys Ser Cys His Tyr Pro Asn Glu Val
            180                 185                 190

Ile Ala Thr Arg Lys Gly Ser Pro Leu Leu Ile Gly Val Lys Ser Glu
            195                 200                 205

Lys Lys Leu Lys Val Asp Phe Val Asp Val Glu Phe Pro Glu Glu Asn
            210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
```

```
                     245                 250                 255
Asn Leu Leu Pro Ile Ala Ala Asn Glu Phe Asn Leu Arg His Ser Gln
                260                 265                 270

Ser Arg Ala Phe Leu Ser Glu Asp Gly Ser Pro Thr Pro Val Glu Phe
            275                 280                 285

Phe Val Ser Ser Asp Ala Ala Ser Val Val Lys His Thr Lys Lys Val
290                 295                 300

Leu Phe Leu Glu Asp Asp Asp Trp Ala His Ile Tyr Asp Gly Glu Leu
305                 310                 315                 320

His Ile His Arg Ser Arg Arg Glu Val Gly Ala Ser Met Thr Arg Ser
                325                 330                 335

Ile Gln Thr Leu Glu Met Glu Leu Ala Gln Ile Met Lys Gly Pro Tyr
                340                 345                 350

Asp His Phe Met Gln Lys Glu Ile Tyr Glu Gln Pro Glu Ser Thr Phe
            355                 360                 365

Asn Thr Met Arg Gly Arg Ile Asp Tyr Glu Asn Asn Lys Val Ile Leu
        370                 375                 380

Gly Gly Leu Lys Ala Trp Leu Pro Val Val Arg Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
            420                 425                 430

Ser Asp Phe Leu Asp Arg Lys Cys Pro Val Ile Arg Asp Asp Val Cys
        435                 440                 445

Val Phe Val Ser Gln Ser Gly Glu Thr Ala Asp Thr Met Leu Ala Leu
    450                 455                 460

Asn Tyr Cys Leu Glu Arg Gly Ala Leu Thr Val Gly Ile Val Asn Ser
465                 470                 475                 480

Val Gly Ser Ser Ile Ser Arg Val Thr His Cys Ser Val His Ile Asn
                485                 490                 495

Ala Gly Pro Glu Ile Gly Val Ala Ser Thr Lys Ala Tyr Thr Ser Gln
            500                 505                 510

Tyr Ile Ala Leu Val Met Phe Ala Leu Ser Leu Ser Asp Asp Arg Val
        515                 520                 525

Ser Lys Ile Asp Arg Arg Ile Glu Ile Gln Gly Leu Lys Leu Ile
    530                 535                 540

Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Gly
                565                 570                 575

Arg Gly Tyr Gln Phe Ala Ala Ala Leu Glu Gly Ala Leu Lys Ile Lys
            580                 585                 590

Glu Ile Ser Tyr Met His Ser Glu Gly Val Leu Ala Gly Glu Leu Lys
        595                 600                 605

His Gly Val Leu Ala Leu Val Asp Glu Asn Leu Pro Ile Ile Ala Phe
    610                 615                 620

Gly Thr Arg Asp Ser Leu Phe Pro Lys Val Val Ser Ser Ile Glu Gln
625                 630                 635                 640

Val Thr Ala Arg Lys Gly His Pro Ile Ile Cys Asn Glu Asn Asp
                645                 650                 655

Glu Val Trp Ala Gln Lys Ser Lys Ser Ile Asp Leu Gln Thr Leu Glu
            660                 665                 670
```

```
Val Pro Gln Thr Val Asp Cys Leu Gln Gly Leu Ile Asn Ile Ile Pro
            675                 680                 685

Leu Gln Leu Met Ser Tyr Trp Leu Ala Val Asn Lys Gly Ile Asp Val
        690                 695                 700

Asp Phe Pro Arg Asn Leu Ala Lys Ser Val Thr Val Glu
705                 710                 715
```

<210> SEQ ID NO 8
<211> LENGTH: 717
<212> TYPE: PRT
<213> ORGANISM: Artificial Sequence
<220> FEATURE:
<223> OTHER INFORMATION: GFA-m16 mutant from Saccharomyces cerevisiae

<400> SEQUENCE: 8

```
Met Cys Gly Ile Phe Gly Tyr Cys Asn Tyr Leu Val Glu Arg Ser Arg
1               5                  10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Asp Glu Ala Asp
        35                  40                  45

Ser Thr Phe Ile Tyr Lys Gln Ile Gly Lys Val Ser Ala Leu Lys Glu
    50                  55                  60

Glu Ile Thr Lys Gln Asn Pro Asn Arg Asp Val Thr Phe Val Ser His
65                  70                  75                  80

Cys Gly Ile Ala His Thr Arg Trp Ala Thr His Gly Arg Pro Glu His
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
    130                 135                 140

Ala Lys Leu Tyr Leu His Leu Tyr Asn Thr Asn Leu Arg Asn Gly His
145                 150                 155                 160

Asp Leu Asp Phe His Glu Leu Thr Lys Leu Val Leu Glu Leu Glu
                165                 170                 175

Gly Ser Tyr Gly Leu Leu Cys Lys Ser Cys His Tyr Pro Asn Glu Val
            180                 185                 190

Ile Ala Thr Arg Lys Gly Ser Pro Leu Leu Ile Gly Val Lys Ser Glu
        195                 200                 205

Lys Lys Leu Lys Val Asp Phe Val Asp Val Glu Phe Pro Glu Glu Asn
    210                 215                 220

Ala Gly Gln Pro Glu Ile Pro Leu Lys Ser Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Ile Ala Ala Asn Glu Phe Asn Leu Arg His Ser Gln
            260                 265                 270

Ser Arg Ala Phe Leu Ser Glu Asp Gly Ser Pro Thr Pro Val Glu Phe
        275                 280                 285

Phe Val Ser Ser Asp Ala Ala Ser Val Val Lys His Thr Lys Lys Val
    290                 295                 300

Leu Phe Leu Glu Asp Asp Asp Leu Ala His Ile Tyr Asp Gly Glu Leu
305                 310                 315                 320
```

```
His Ile His Arg Ser Arg Arg Glu Val Gly Ala Ser Met Thr Arg Ser
                325                 330                 335

Ile Gln Thr Leu Glu Met Glu Leu Ala Gln Ile Met Lys Gly Pro Tyr
                340                 345                 350

Asp His Phe Met Gln Lys Glu Ile Tyr Glu Gln Pro Glu Ser Thr Phe
                355                 360                 365

Asn Thr Met Arg Gly Arg Ile Asp Tyr Glu Asn Asn Lys Val Ile Leu
                370                 375                 380

Gly Gly Leu Lys Ala Trp Leu Pro Val Val Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
                420                 425                 430

Ser Asp Phe Leu Asp Arg Lys Cys Pro Val Phe Arg Asp Asp Val Cys
                435                 440                 445

Val Phe Val Ser Gln Ser Gly Glu Thr Ala Asp Thr Met Leu Ala Leu
                450                 455                 460

Asn Tyr Cys Leu Glu Arg Gly Ala Leu Thr Val Gly Ile Val Asn Ser
465                 470                 475                 480

Val Gly Ser Ser Ile Ser Arg Val Thr His Cys Gly Val His Ile Asn
                485                 490                 495

Ala Gly Pro Glu Ile Gly Val Ala Ser Thr Lys Ala Tyr Thr Ser Gln
                500                 505                 510

Tyr Ile Ala Leu Val Met Phe Ala Leu Ser Leu Ser Asp Asp Arg Val
                515                 520                 525

Ser Lys Ile Asp Arg Arg Ile Glu Ile Ile Gln Gly Leu Lys Leu Ile
                530                 535                 540

Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Leu Gly
                565                 570                 575

Arg Gly Tyr Gln Phe Ala Ala Ala Leu Glu Gly Ala Leu Lys Ile Lys
                580                 585                 590

Glu Ile Ser Tyr Met His Ser Glu Gly Val Leu Ala Gly Glu Leu Lys
                595                 600                 605

His Gly Val Leu Ala Leu Val Asp Glu Asn Leu Pro Ile Ile Ala Phe
                610                 615                 620

Gly Thr Arg Asp Ser Leu Phe Pro Lys Val Val Ser Ser Ile Glu Gln
625                 630                 635                 640

Val Thr Ala Arg Lys Gly His Pro Ile Ile Cys Asn Glu Asn Asp
                645                 650                 655

Glu Val Trp Ala Gln Lys Ser Lys Ser Ile Asp Leu Gln Thr Leu Glu
                660                 665                 670

Val Pro Gln Thr Val Asp Cys Leu Gln Gly Leu Ile Asn Ile Ile Pro
                675                 680                 685

Leu Gln Leu Met Ser Tyr Trp Leu Ala Val Asn Lys Gly Ile Asp Val
                690                 695                 700

Asp Phe Pro Arg Asn Leu Ala Lys Ser Val Thr Val Glu
705                 710                 715
```